United States Patent [19]

Pescatore

[11] Patent Number: 4,501,265
[45] Date of Patent: Feb. 26, 1985

[54] APPLICATOR HEAD FOR ELECTROMAGNETIC TREATMENT OF AN AFFLICTED BODY REGION

[75] Inventor: Eugene A. Pescatore, Elmwood Park, N.J.

[73] Assignee: Electro-Biology, Inc., Fairfield, N.J.

[21] Appl. No.: 452,421

[22] Filed: Dec. 23, 1982

[51] Int. Cl.³ .............................................. A61N 1/40
[52] U.S. Cl. .................................... 128/1.5; 128/82.1; 128/419 F
[58] Field of Search .................... 128/1.5, 82.1, 419 F

[56] References Cited
FOREIGN PATENT DOCUMENTS 51997 7/1936 Denmark ............................ 128/1.5
2822285 11/1979 Fed. Rep. of Germany ....... 128/1.5
WO82/3178 9/1982 PCT Int'L Appl. ................ 128/1.5

Primary Examiner—Kyle L. Howell
Assistant Examiner—John C. Hanley
Attorney, Agent, or Firm—Hopgood, Calimafde, Kalil, Blaustein & Judlowe

[57] ABSTRACT

The invention contemplates a specific coil configuration adapted for application to particular regions of the body, for use in treating a selected such region with pulsed electromagnetic signals which are induced within the body as electric voltage and concomitant current signals which alter the growth, repair and maintenance behavior of living tissues and cells within the body region under treatment.

10 Claims, 8 Drawing Figures

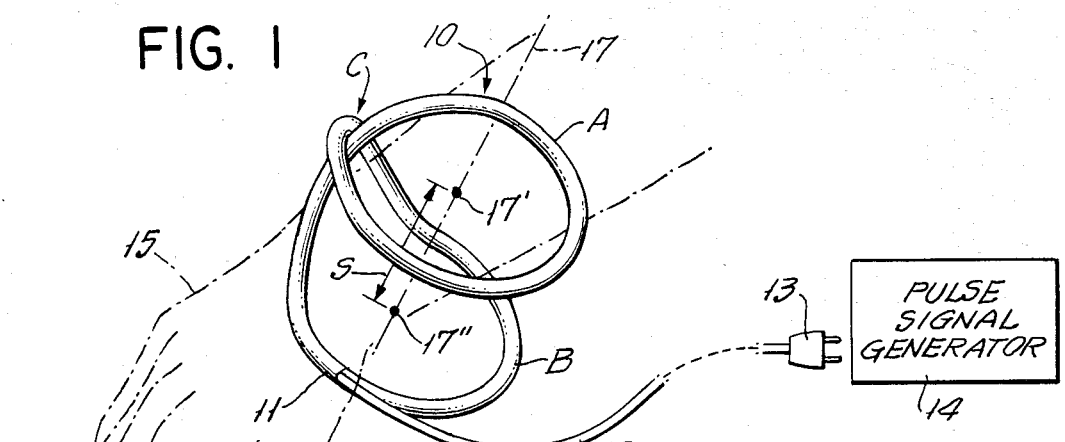
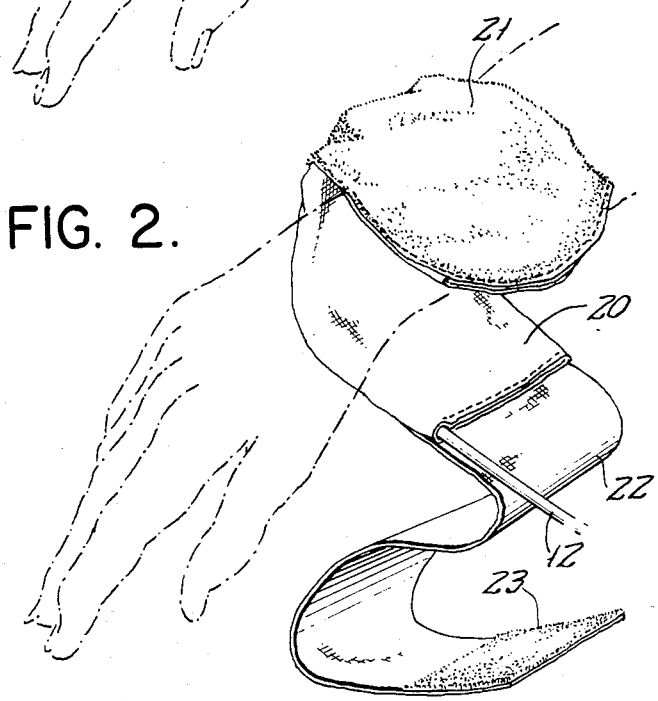
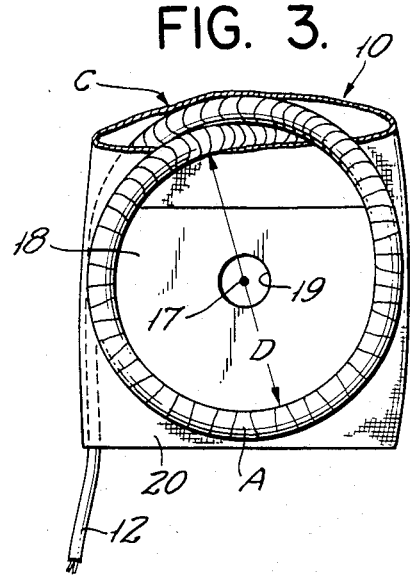
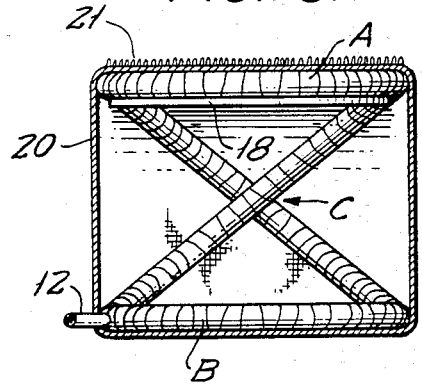
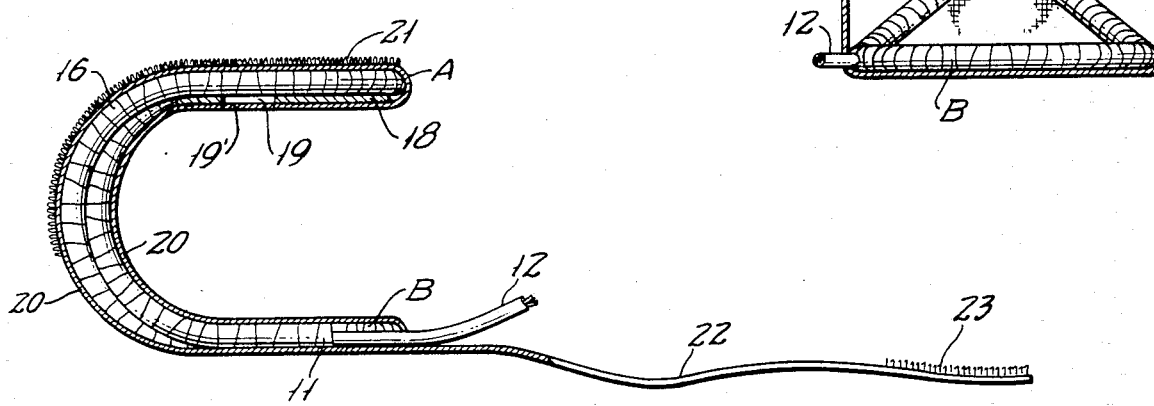

APPLICATOR HEAD FOR ELECTROMAGNETIC TREATMENT OF AN AFFLICTED BODY REGION

BACKGROUND OF THE INVENTION

This invention relates to the treatment of living tissues and/or cells by altering their interaction with charged species in their environment. More particularly, the invention relates to an electromagnetic body-treatment device for surgically non-invasive modification of the growth, repair and maintenance behavior of living tissues and cells by a specific and selective change in electrical environment.

Ryaby, et al., U.S. Pat. Nos. 4,105,017, 4,266,532 and 4,266,533 describe means for effecting surgically non-invasive direct inductive coupling to an afflicted body region, whereby one or more electric voltage and concomitant current signals conform to a highly specific pattern and have been found to develop therapeutically beneficial treatment of the afflicted region, as for example in the enhancement of repair of bone fractures, non-unions, and the like. In general, the involved treatment head or heads have involved one or more large coils, which have served well for the treatment of large-member bones, as in leg regions. And various special-purpose coil and head configurations have been disclosed for specific treatments. In general, it may be said that it has been preferred practice to employ a treatment-head configuration in which two like coils are electrically connected in flux-aiding relation and have flexibly articulated connection to enable strapped application on opposite sides of an afflicted limb, and with the coils on a common axis of magnetic-flux development through the afflicted region. However, for certain injuries, such as bone injury in the scaphoid region of the arm, it becomes very awkward, bothersome, and inconvenient to use the conventional articulated-coil technique, in that use of the arm must be severely curtailed, due primarily to treatment-head considerations.

BRIEF STATEMENT OF THE INVENTION

It is an object of the invention to provide a new approach to treatment-head design in equipment of the character indicated, with a view to reducing bulk and simplifying application to an afflicted region of the body.

It is a specific object to provide an improved treatment head of the character indicated for application to scaphoid and other outer-arm regions.

The invention achieves these objects with a single multi-turn electrical coil which is so bundled and deformed as to establish two like loops in spaced substantially parallel planes, with crossover of equally spaced regions of the coil, the crossover regions being a significant element in the relatively rigid positional spacing of the two loops. Upon exciting the coil with pulsed electrical signals as disclosed in said Ryaby, et al. patents, one obtains a flux-aiding coaction between the two loops whereby relatively uniform flux distribution characterizes the region bounded by and between the loops.

In one embodiment, fabric separately encases the two loops and the crossover region by which they are integrally connected, so that the treatment head is of generally U-shape, for side-entry of the afflicted region via the open end of the U-shape; a flexible strap and fastener selectively closes the open end of the U-shape. In another embodiment, fabric encasement of the coils establishes an overall tubular configuration for limb insertion within and along the length of the tube, the respective loops of the coil defining the shape of the ends of the tubular configuration.

DETAILED DESCRIPTION

The invention will be illustratively described in detail, in conjunction with the accompanying drawings, in which:

FIG. 1 is a simplified view in perspective to illustrate coil formation of the invention;

FIG. 2 is a view similar to FIG. 1, but including fabric encasement used with the coil of FIG. 1;

FIG. 3 is a plan view of the coil formation of FIG. 1;

FIGS. 4 and 5 are side and end views of the coil formation of FIG. 1, to reveal the U-shape and including a sectionalized showing of the fabric encasement of FIG. 1;

Figure 6:
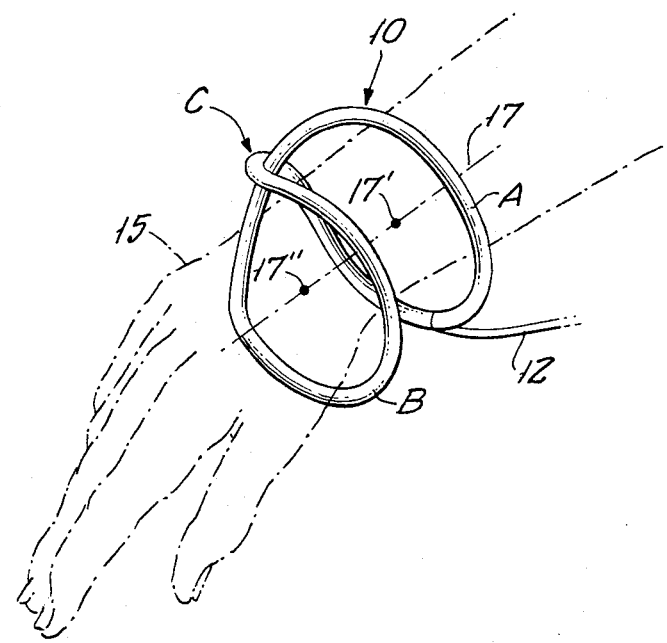
FIG. 6 is a view similar to FIG. 1, to illustrate another mode of use of the coil formation of FIG. 1.

Referring initially to FIG. 1, the invention is shown in application to a single coil 10 of multiple turns of insulated wire, the ends of the coil having lead connection at 11 to a flexible cable 12 for removable connection via a plug 13, to a pulse-signal generator 14. Such a signal generator and the character of signals produced thereby have been described in said Ryaby, et al. patents, so that further description thereof is not now needed.

For treatment of bone injury in the scaphoid region, as suggested by the phantom outline 15 of an arm in FIG. 1, the single coil 10 is suitably of about 60 turns of B & S gauge-12 copper wire, initially wound to a diameter of 23 cm and then bundled. Diametrically opposed locations of the bundle are then selected for crossover adjacency, and the peripherally equal segments bounded by said locations are subjected to a half-turn twist, resulting in an intermediate, substantially figure-eight appearance of the bundle. The figure-eight appearance defines two equal loops A-B, connected by the crossover region (C), and the figure-eight bundle is further bent so that the loops A-B are in spaced substantially parallel relation, with integral spacing and semi-rigid retention of the spacing of loops A-B, via crossover region C. Bending into the indicated shape will be understood to be performed against one or more suitable templates, and shape retention and bundle integrity are served by taped wrap of the bundle, as by electrician's adhesive tape 16 (FIGS. 4 and 5). The resulting configuration, for the indicated initial winding to 23 cm diameter, establishes loops A-B of 3.75-inch mean diameter and at 3.5-inch mean spacing.

The above-described formative steps are seen to produce an integral single-coil structure which is the electrical and magnetic equivalent of two coils, formed by the respective loops A-B, which are necessarily of effective diameter D (FIG. 3), less than half the diameter to which the single coil was originally developed. Upon excitation, each of the loops A-B performs as a separate coil on a common axis 17 of magnetic-flux development, and by reason of the half-turn at crossover region C, the flux development at A-B is flux-aiding. For purposes of better visualizing the flux-development axis 17 in FIG. 1, separate intercepts are indicated at 17'-17" where axis 17 passes through the respective planes of loops A and B. And, for reasons indicated in conjunction with FIG. 13 of said Ryaby, et al. patents '532 and '533, it is preferred that the spacing S between loops A-B (i.e., between intercepts 17'-17") be substantially equal to or less than the effective diameter D of loops A-B, thus promoting relative uniformity of flux density in a generally cylindrical volume of treatment zone within and between loops A-B.

As best seen in the side view of FIG. 4, the described deformation of coil 10 establishes a generally U-shaped profile wherein loops A and B are the arms of the U-shape so that application to an afflicted limb region can be laterally of the axis 17, via the open end of the U-shape. In the case of bone fracture, the orthopedic surgeon will first have prepared the limb for recovery, by conventional application of a cast, and in doing so, he will preferably have integrated a post into the cast, with the post projecting a short distance outside the cast, as a means of reference to assure desired alignment for electromagnetically applied therapy. The provision of such a post or locating key, for inclusion in the cast and for coaction with an electromagnetic treatment head, is described in connection with FIGS. 7A and 8 in said Ryaby, et al. '532 patent; and similar locating coaction with the treatment head of the present invention is available by providing a rigid non-conductive plate 18, as of fiberglass-reinforced epoxy, bonded to the inner side of one of the loops, here shown as loop A. Plate 18 is seen in FIG. 4 to be centrally apertured at 19, on axis 17, for the keying or locating purposes indicated and described at greater length in the Ryaby, et al. '532 patent.

For cosmetic and better-handling purposes, it is preferred to encase the described structure in a fabric material 20. Such material may be a length of woven or knitted tubing or hose, into which the described U-shape is inserted, to provide separate fabric encasing of the respective loops A-B and of the crossover connection therebetween, the ends of the encasement being closed as by stitching and allowing only for external availability of the lead cable 12 and its plug 13. It is preferred that such encasing fabric be rugged, as for example of woven glass fiber, and that separable fastening means be carried by fabric 20 for selective closure of the open end of the U-shape. Preference is indicated that hook and loop materials, known by the trademark Velcro, be used for this purpose. Therefore, as shown, the outer exposed surface of the fabric encasement 20 carries a finishing ply of loop material 21, and a flexible belt 22 extending from the encasement material at one of the ends of the U-shape carries an inner ply or facing 23 of hook material, it being noted that the locale of leadcable (12) access is at lateral offset from belt 22.

In placing the described treatment head over a cast of the character indicated, entry is via the open end of the U-shape, until engagement of the locating post or key of the cast, in the coacting aperture 19 of the locating plate 18, via a corresponding aperture 19' in material 20, the latter being locally bonded to plate 19. Once thus located, the coil structure A-B-C is sufficiently compliant to permit compression of the arms of the U-shape against the cast, and retention of the compression via lapped engagement of hook material 23 over loop material 21, to hold a closure of the U-shape.

The described application of the treatment head is really only needed during the intermittent times of electromagnetic therapy. Therefore, the hook and loop closure may be disengaged and the treatment head removed, during periods between treatments, it being understood that the patient may use his free arm for removal and for reapplication of the treatment head, when needed.

Figure 7:
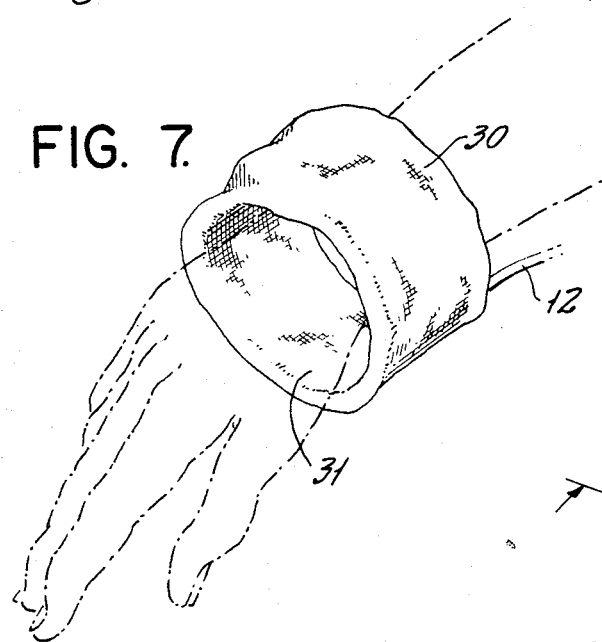
FIG. 7 is a view similar to FIG. 6, but showing modified fabric encasement used with the coil of FIG. 1, to serve the mode of use of FIG. 6.
Figure 8:
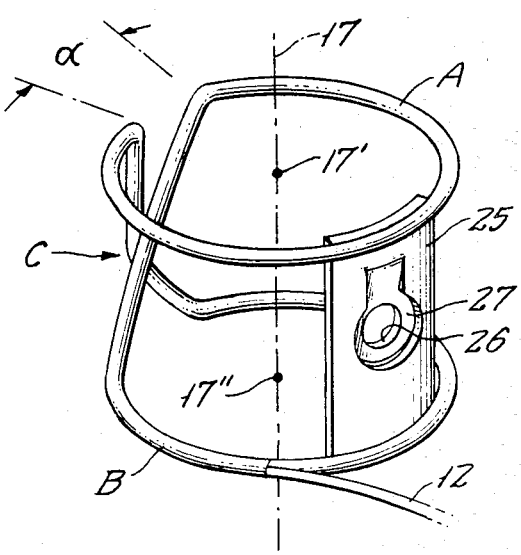
FIG. 8 is a view similar to FIG. 1 to illustrate modification of FIGS. 1 and 6.

FIGS. 6, 7 and 8 illustrate another mode of use of the coil configuration A-B-C of FIG. 1, wherein the axis 17 of magnetic-flux development is oriented longitudinal to the afflicted limb 15. For such purposes, the plate 18 of FIG. 4 is replaced by a plate 25 (FIG. 8) which is rigid to at least one of the loops A-B and which extends therebetween, preferably at a location diametrically opposite the crossover location C. As shown, plate 25 is rigid to both loops A-B, and its locating aperture 26 is on a spring tab 27, the latter being defined by horseshoe-piercing of plate 25. Upon longitudinal insertion of limb 15 and its cast into such a treatment head, manipulation is continued until tab aperture 26 registers with the locating key of the cast, whereupon tab 27 resiliently snaps in to retain the correct location, i.e., in which the afflicted region is longitudinally centered between loops A-B.

As with the embodiment of FIGS. 1 to 5, it is preferred that the treatment head in the mode of FIGS. 6 to 8 be fabric-encased, as the same appears in FIG. 7, wherein an outer sleeve 30 will be understood to surround both loops A and B, and the crossover region C; and an inner sleeve 31 lines the generally cylindrical space within loops A-B and region C. This result is accomplished either by stitching the ends of sleeves 30-31 to each other to complete the casing, or by employing a single sleeve which is outside-out at region 30 and tucked into and back on itself to be outside-in, at region 31, the remaining ends of regions 30-31 being then peripherally stitched to each other to complete the encasing. Again, as at 19-19' in FIG. 4, the inner region 31 will be understood to be apertured (not shown) in register with tab aperture 26 and to be bonded to tab 27 around such aperture.

The described structure will be seen to meet stated objects. Bulk is reduced and electrical connections are simplified by reliance upon a single multi-turn coil 10. The initially wound diameter is to be understood to be purely illustrative, in that different initially wound diameters will clearly permit development of different effective loop diameters D and spacings S, as appropriate for size of cast and limb or other body region to be treated; a range of 18 cm to 25 cm initially wound diameters has, to date, been found to serve special applications of the character indicated. Nor is the wire size or number of turns of the coil to be considered limiting, because these factors will be understood to be as appropriate for the particular signal levels delivered by generator 14, in order to develop desired specific induced electrical voltage and concomitant current signals within the afflicted body region under treatment.

While the invention has been described in detail for a preferred form and modes of use, it will be understood that modifications may be made without departure from the scope of the invention. For example, as illustrated in FIG. 8, the loops A-B may each describe almost a complete circular course, interrupted only to minimal angular extent α to accommodate the crossover region. It may be observed, however, that with such angular extent α as large as almost 90 degrees (as the same appears by inspection of FIGS. 1 and 6), the treatment head is an effective instrumentality for transducing the pulsed-signal output of generator 14 into therapeutically beneficial induced voltages and concomitant currents within the body zone under treatment.

What is claimed is:

1. An electromagnetic body-treatment device for surgically non-invasive modification of the growth, repair and maintenance behavior of living tissues and cells by a specific and selective change in electrical environment, comprising a single multi-turn electrical coil of initially generally circular configuration, said coil having a flexible external lead-cable connection and said coil being deformed into a body-adapting retaining figure-eight configuration to thus define two loops with a generally central crossover integrally connecting said loops, the generally central crossover region being generally arcuately bent to provide a relatively rigid positioner of said two loops in spaced substantially parallel planes wherein the effective local diameter of each of said loops substantially equals or exceeds the effective spacing between said planes, said loops being about a single axis of flux development that is substantially normal to said planes, and means connected to said cable connection for electrically exciting said single coil with a succession of low-voltage unidirectional asymmetrical pulses; whereby, upon insertion of an afflicted body region in the space between said loops, said smaller loops coact in flux-aiding fashion to establish substantially uniform flux distribution in the afflicted body region.

2. The device of claim 1, and including a fabric enclosure separately around each of said loops and around the crossover region between said loops, thereby presenting an overall U-shape wherein the afflicted body region may be laterally inserted through the open side of the U-shape.

3. The device of claim 2, and including releasable means carried by said fabric enclosure for selectively closing the open side of the U-shape.

4. The device of claim 3, in which said releasable means includes hook and loop materials, wherein one of said materials characterizes the exterior of said fabric closure at one of said coil loops, and wherein a flexible strap connection to the fabric enclosure at the other of said coil loops includes the other of said materials on its inner face.

5. The device of claim 4, in which the loop material is on the exterior of said fabric enclosure and in which the hook material is on the inner face of said strap.

6. The device of claim 1, and including a fabric enclousre including an outer tubular course encompassing said loops and crossover along the flux-development axis and an inner tubular course within both loops and peripherally connected to the respective ends of said outer tubular course.

7. The device of claim 1, and a plate of non-conducting material fixedly carried by and spanning one of said loops, said plate having a central opening adapted for coil-locating engagement with a locating-post formation of an orthopedic cast around the afflicted body region.

8. The device of claim 1, and a plate of non-conducting material fixedly carried by at least one of said loops and spanning substantially the distance to the other of said loops, said plate having an opening adapted for coil-locating engagement with a locating-post formation of an orthopedic cast around the afflicted body region.

9. An electromagnetic body-treatment device for surgically non-invasive modification of the growth, repair and maintenance behavior of living tissues and cells by a specific and selective change in electrical environment, comprising a single multiple-turn electrical coil with a flexible external lead-cable connection, the turns of said coil being bound to define a single bundle of first peripheral extent, said bundle being twisted to the extent of one half turn with bundle-segment crossover at equal half points of said peripheral extent, a first generally circular loop of said bundle of less than half said extent on one side of said crossover, a second loop of less than half said extent on the other side of said crossover, means including the region of said crossover retaining said loops in spaced relation on a flux-development axis through both loops, the effective local diameter of said loops substantially equalling or exceeding the effective spacing between said planes, and means including said cable connection for electrically exciting said single coil with a succession of low-voltage unidirectional asymmetrical pulses.

10. An electromagnetic body-treatment device for surgically non-invasive modification of the growth, repair and maintenance behavior of living tissues and cells by a specific and selective change in electrical environment, comprising a single multi-turn electrical coil of initially generally circular configuration, said coil having a flexible external lead-cable connection and said coil being deformed into a body-adapting retaining figure-eight configuration to thus define two loops with a generally central crossover integrally connecting said loops, the generally central crossover region being generally arcuately bent to provide a relatively rigid positioner of said two loops in spaced substantially parallel planes wherein the effective local diameter of each of said loops and the effective spacing between said planes are of comparable magnitude, said loops being about an axis of flux development that is substantially normal to said planes, and means connected to said cable connection for electrically exciting said single coil with a succession of low-voltage unidirectional asymmetrical pulses; whereby, upon insertion of an afflicted body region in the space between said loops, said smaller loops coact in flux-aiding fashion to establish therapeutically beneficial flux distribution in the afflicted body region.

* * * * *